United States Patent [19]

Gsell et al.

[11] Patent Number: 5,258,127
[45] Date of Patent: Nov. 2, 1993

[54] LEUCOCYTE DEPLETING FILTER DEVICE AND METHOD OF USE

[75] Inventors: Thomas C. Gsell, Glen Cove; Thomas Bormann, Seaford; Vlado I. Matkovich, Glen Cove, all of N.Y.

[73] Assignee: Pall Corporation, Glen Cove, N.Y.

[21] Appl. No.: 756,567

[22] Filed: Sep. 11, 1991

Related U.S. Application Data

[63] Continuation-in-part of Ser. No. 558,468, Jul. 25, 1990, abandoned.

[51] Int. Cl.⁵ .............. B01D 37/00; B01D 39/04; B01D 19/00
[52] U.S. Cl. .................. 210/767; 210/188; 210/436; 210/493.1; 210/497.01; 210/503; 210/508; 427/569; 604/126; 252/321; 95/260; 96/204
[58] Field of Search ............. 210/691, 750, 767, 788, 210/805, 188, 436, 422, 512.1, 489, 492, 496, 502.1, 493.1, 497.01, 487, 503, 508, 748; 427/40, 41, 569; 55/159, 185, 186, 187, 204, 178; 604/4, 5, 122, 126; 428/409

[56] References Cited

U.S. PATENT DOCUMENTS

| | | |
|---|---|---|
| 3,383,163 | 5/1968 | Menashi . |
| 3,448,041 | 6/1969 | Swank .................. 210/496 |
| 3,593,854 | 7/1971 | Swank .................. 210/436 |
| 3,765,536 | 10/1973 | Rosenberg ............ 210/446 |
| 4,087,363 | 5/1978 | Rosenmeyer et al. .. 210/315 |
| 4,116,845 | 9/1978 | Swank .................. 210/446 |
| 4,157,967 | 6/1979 | Meyst et al. ........... 210/449 |
| 4,214,014 | 7/1980 | Höfer et al. ............ 427/40 |
| 4,261,806 | 4/1981 | Asai et al. ............. 204/168 |
| 4,445,991 | 5/1984 | Arbit .................... 204/168 |
| 4,488,954 | 12/1984 | Hatada et al. ......... 204/169 |
| 4,572,724 | 2/1986 | Rosenberg et al. .... 55/159 |
| 4,701,267 | 10/1987 | Watanabe et al. ..... 210/806 |
| 4,743,371 | 5/1988 | Servas et al. .......... 210/188 |
| 4,828,698 | 5/1989 | Jewell et al. .......... 210/266 |
| 4,845,132 | 7/1989 | Masuoka et al. ...... 210/490 |
| 4,861,617 | 8/1989 | Pall et al. .............. 427/2 |
| 4,880,548 | 11/1989 | Pall et al. .............. 210/767 |
| 4,923,620 | 5/1990 | Pall ...................... 210/767 |
| 4,925,572 | 5/1990 | Pall ...................... 210/767 |
| 4,933,092 | 6/1990 | Aunet et al. .......... 210/729 |
| 4,936,998 | 6/1990 | Nishimura et al. .... 210/638 |
| 4,948,628 | 8/1990 | Montgomery et al. . 427/39 |
| 4,963,260 | 10/1990 | Naoj et al. ............ 210/446 |
| 4,985,153 | 1/1991 | Kuroda et al. ........ 210/782 |
| 5,028,332 | 7/1991 | Ohnishi ................. 210/500.34 |

FOREIGN PATENT DOCUMENTS 0315022 5/1989 European Pat. Off. .
0370584 5/1990 European Pat. Off. .

OTHER PUBLICATIONS

Pall RC100-Leucocyte Removal Filter for Blood Transfusion—Pall Biomedical Products Corporation (1988).
Pall PL100-Leukocyte Removal Filter for Platelet Transfusion—Pall Biomedical Products Corporation (1988).
"The Pall Blood Filter for Extracorporeal Service", Pall et al., Mar. 1984, E34C.
"Intersept Extracorporeal Blood Filters", Johnson & Johnson Co.

(List continued on next page.)

*Primary Examiner*—Robert A. Dawson
*Assistant Examiner*—Sun U. Kim
*Attorney, Agent, or Firm*—Leydig, Voit & Mayer

[57] ABSTRACT

Leucocyte depletion filter assemblies decrease the leucocyte content of a biological fluid in an extracorporeal circuit. These filter assemblies are suitable for use in an extracorporeal circuit. Methods for removing leucocytes and other deleterious matter are also disclosed. The removal medium used in these assemblies and methods may be pleated structures which have been subjected to gas plasma treatment, improving the amount of leucocytes removed and increasing the amount of platelets which pass through the medium.

32 Claims, 2 Drawing Sheets

OTHER PUBLICATIONS

"Bibliography of Swank Blood Filters for Extracorporeal Circulation", Swank et al.

"The Pall EC Plus Filter", A New Generation Extracorporeal Filter, Pall et al., pp. 3–7.

"AutoVent-SP", Auto-Venting Blood Filter, Biomedical Products Corporation, Pall et al.

"Disposable Filter for Microemboli", Journal of the American Medical Association, Patterson et al., Jan. 4, 1971, vol. 215, pp. 76–80.

"Performance Characteristics of Bentley Duraflo II Treated Arterial Filters", Baxter Healthcare Corporation, pp. 3–11.

"Plasma Deposition, Treatment, and Etching of Polymers", Riccardo d'Agostino, Academic Press, Inc., 1990, pp. 463–516.

S. Karger, "Journal of Blood Transfusion", etc., Vox Sanguinis, Vox Sang.23: (1972), pp. 308–320.

LEUCOCYTE DEPLETING FILTER DEVICE AND METHOD OF USE

This application is a continuation-in-part application of U.S. application Ser. No. 07/558,468, filed Jul. 27, 1990, now abandoned.

TECHNICAL FIELD

The invention relates to porous media for removing leucocytes and other deleterious material from biological fluids such as blood. For example, the invention relates to the removal of leucocytes from blood in an extracorporeal circuit.

BACKGROUND OF THE INVENTION

Extracorporeal circuits, and the use of a filtration device in such a circuit, are well known and are commonly used therapeutically or clinically to prevent or reduce damage caused by leucocyte activation as a result of leucocyte contact with foreign matter, as well as a number of other diseases and conditions.

Leucocytes are a type of blood cell in the immune system which constitute the principal means of defense against antigens, such as infection by pathogenic microorganisms and viruses, and probably also against most cells that undergo transformation into cancer cells. Leucocyte activation, the leucocytic monitoring and arming functions, proceeds from a complex series of biochemical interactions, typically terminating in engulfing and digesting the antigen. If the leucocytes have been so activated, but lack an appropriate antigenic target, the leucocytes may inflict damage to internal organs, particularly ischemic tissues, i.e., tissues in which no blood is flowing such as the heart and lungs during certain surgical procedures.

Moreover, with increasing frequency, the most common leucocyte, the granulocytic neutrophil, has been implicated as the mediator of tissue destructive events in a variety of disorders, including reperfusion injury, respiratory distress syndromes, rheumatoid arthritis, skin disorders and ulcerative colitis. The commonality which pervades these pathologies is the neutrophil's ability to release a number of agents which can disrupt and destroy normal cellular function, dissolve connective tissue, and cause injury to organs.

It has also been shown that circulating leucocytes contribute to or mediate ischemic and reperfusion injury during organ preservation, particularly following extended preservation of the heart-lung bloc commonly required during cardiopulmonary bypass operations (CPB). Leucocytes have also been associated with increased oxygen radical activity, pulmonary edema, and vasoconstriction.

SUMMARY OF THE INVENTION

According to the present invention, a filter assembly for removing leucocytes and other deleterious matter from a liquid, such as blood, generally comprises a housing and a fibrous medium. The housing has an inlet and an outlet and defines a liquid flow path between the inlet and the outlet. The fibrous medium is positioned inside the housing across the liquid flow path and includes a fibrous structure for decreasing the leucocyte content of the liquid, typically at a flow rate greater than about 25 milliliters per minute.

Filter assemblies which embody the invention may include a filter element having one or more of the following characteristics: a hollow, generally cylindrical configuration; a total fibrous surface area greater than about 1.5 square meters; a critical wetting surface tension (CWST) of 53 dynes per centimeter or more, and fibers which have been subjected to gas plasma treatment The filter assemblies may have a pleated structure, a total hold-up volume up to about 400 cubic centimeters, and may further comprise a porous degassing element for removing gas from the liquid, a liquophobic membrane which allows gas but not liquid to escape from the housing, and/or a vent for removing gas from the housing The present invention also provides a method for removing leucocytes and other deleterious matter from a liquid, such as blood. The method generally comprises decreasing the leucocyte content of the liquid by passing the liquid through a fibrous medium having one or more of the characteristics noted above. Methods embodying the invention may also include repeatedly recirculating blood through a housing in an extracorporeal circuit; separating gas from the liquid; and/or venting the gas from the housing.

Filter assemblies and methods embodying the present invention are particularly advantageous. They remove leucocytes and leucocyte-type cells very effectively. Leucocytes are not only trapped in the interstices of the fibrous medium, but they also adhere to the surfaces of the fibers in the medium. The fibrous medium provides ample surface area on which the leucocytes can adhere. Having a CWST of 53 dynes per centimeter or greater, the fibrous medium can have a CWST greater than the surface tension of the liquid, allowing the liquid to readily wet the fibrous medium, actively seep into all of the interstices of the filter medium, and completely contact the ample surface area of the fibers.

Filter assemblies and methods embodying the present invention are capable of removing leucocytes while maintaining a large flow of liquid through the pleated fibrous medium for a considerable span of time without clogging or plugging Conventional filters may remove leucocytes at low flows, e.g., 5–10 milliliters per minute, but embodiments of the present invention are capable of removing leucocytes at much greater flow rates, even hundreds of times greater. Also, the pleated fibrous medium, treated as noted below, not only permits the passage of a greater proportion of platelets than heretofore possible, but also selectively increases the percentage of neutrophils removed from the liquid. As noted previously, because the CWST of the fibrous medium can be 53 dynes per centimeter or greater and, therefore, can be greater than the surface tension of the liquid, the liquid flows through the medium with minimal resistance due to the effects of surface tension and resists plugging or clogging. Thus, although embodiments of the present invention are nonetheless effective at low flow rates, they are capable of removing leucocytes at very large flow rates for extended periods of time. For example, leucocytes may be removed from a liquid such as blood at a flow rate up to six liters per minute for three to four hours and, in some cases up to ten hours, without clogging or plugging.

Filter assemblies and methods which incorporate the gas plasma treatment (GPT) protocol according to the invention provide surprising results. The products of the present invention have very low amounts of leachable matter that could contaminate the liquid being filtered. Further, it was found that surfaces prepared by the GPT method according to the invention have low adhesiveness for platelets and thus pass a larger proportion of the platelets through the filter, a characteristic which is highly beneficial, particularly during surgery, collecting and processing donated blood, and other similar protocols. Additionally, the rate of leucocyte removal using GPT treated porous media was higher than for non-GPT treated porous media.

A filter assembly or method embodying the present invention may be used in an extracorporeal circuit, and/or may be employed for therapeutic applications, including but not limited to cardiopulmonary bypass operations or the like, autologous transfusion, leucopheresis, apheresis, or dialysis. Thus, the device and method have application whenever a biological fluid, such as blood or a leucocyte-containing liquid, is brought into contact with external circuitry, and thence returned to the body or specific organs.

A filter assembly or method embodying the present invention may also be used for a number of other therapeutic or surgical protocols, including, but not limited to cardioplegia or coronary perfusion, in order to perfuse and maintain safe levels of metabolic activity within tissues and organs; for myocardial infarcted patients to reduce subsequent damage during reperfusion in the affected heart region; and to reduce or eliminate the deleterious effects attributed to a wide variety of injuries, diseases, or conditions. Passing the patient's blood through a device in accordance with the present invention can be used in clinical or therapeutic regimens in which leucocyte depletion is beneficial. Also, the media embodying the present invention can be used clinically or therapeutically to remove cancer cells and the like which are structurally similar to leucocytes.

DESCRIPTION OF THE EMBODIMENTS

A filter assembly in accordance with the present invention comprises a housing, having an inlet and an outlet, and a pleated porous medium disposed in the housing for decreasing the leucocyte content and removing other deleterious matter from a leucocyte-containing liquid. Biological fluid, as used herein, refers to blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate, platelet-rich plasma, platelet-poor plasma, plasma, or packed red cells; analogous blood products derived from blood or a blood component or derived from bone marrow; and other leucocyte- or leucocyte precursor cell-containing liquids. Deleterious matter, as used herein, includes activated and non-activated leucocytes, fat emboli, microaggregates, lipids, cells which are morphologically similar to leucocytes, cellular material, and other debris. Preferred embodiments of the invention may also comprise a degassing mechanism cooperatively arranged with the housing for removing gaseous emboli from the liquid.

In accordance with the invention, the porous medium may take any of a number of forms, including, for example, a web, matrix, flat sheet, membrane, or in a corrugated or pleated structure. For example, in a preferred embodiment of the present invention, the porous medium may be corrugated to form pleats. The pleated filter medium may have longitudinally extending pleats having peaks. In another form of the invention, the porous medium may include fibers which may be bonded, fused, or otherwise fixed to one another or they may simply be mechanically entwined. In another preferred embodiment, the fiber diameter and/or void spaces may vary in a continuous or stepwise manner.

The filter assembly may be configured in a variety of ways in accordance with the invention. For example, the filter assembly may include a hollow porous medium which may have a cylindrical shape and may be disposed in the housing to filter liquid flowing laterally or radially through the filter element. For example, to filter liquid flowing inside/out through the porous medium, the inlet and outlet of the filter assembly would be arranged to respectively communicate with the interior and exterior of the hollow porous medium.

In the illustrated embodiment, the filter assembly is arranged to filter liquid flowing outside/in through the porous medium. This arrangement is preferred because it provides a porous medium with a large surface area in a compact housing.

Figure 1:
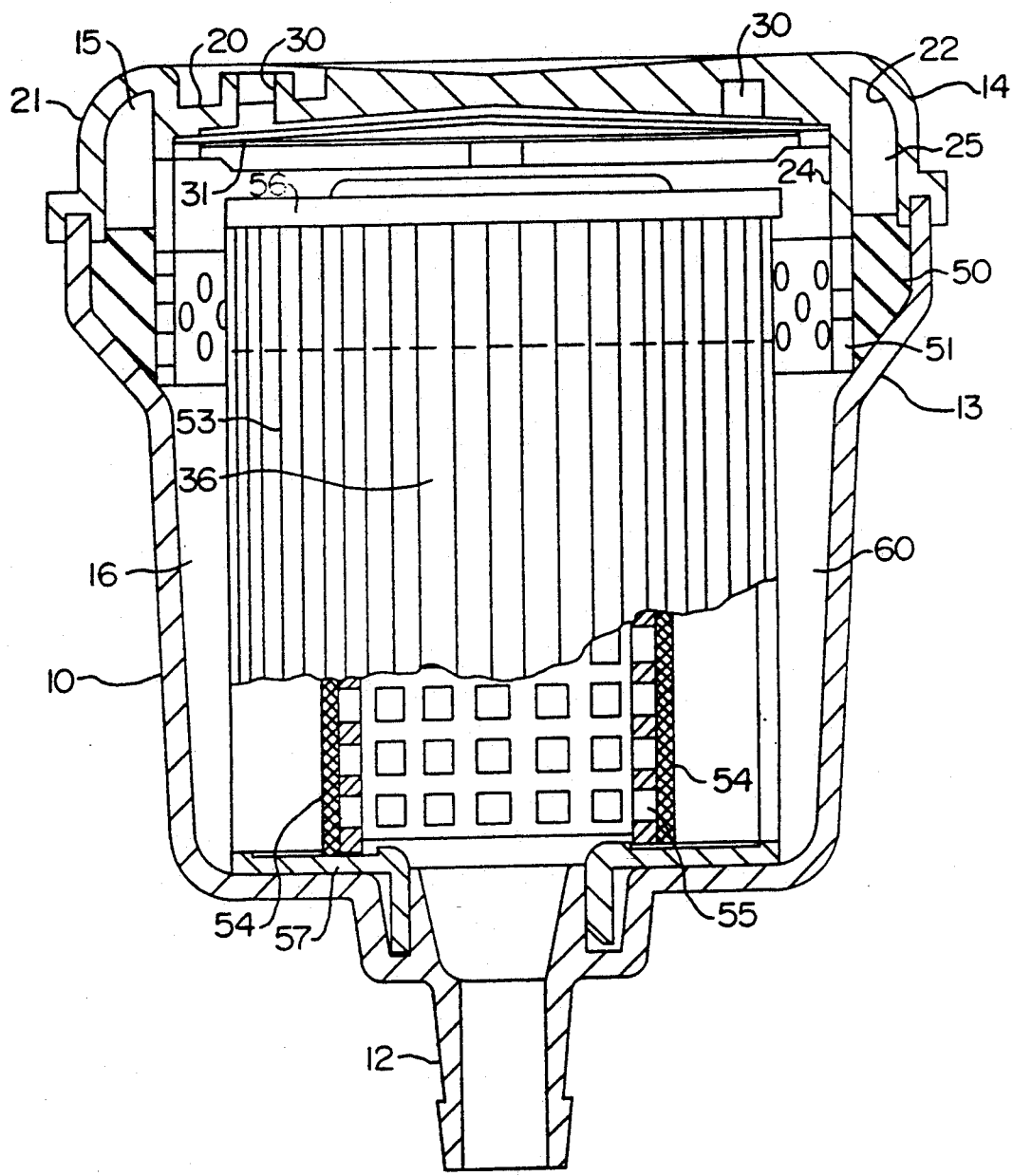
FIG. 1 is a cross section of a typical extracorporeal filter assembly having a pleated porous medium positioned inside a housing.
Figure 2:
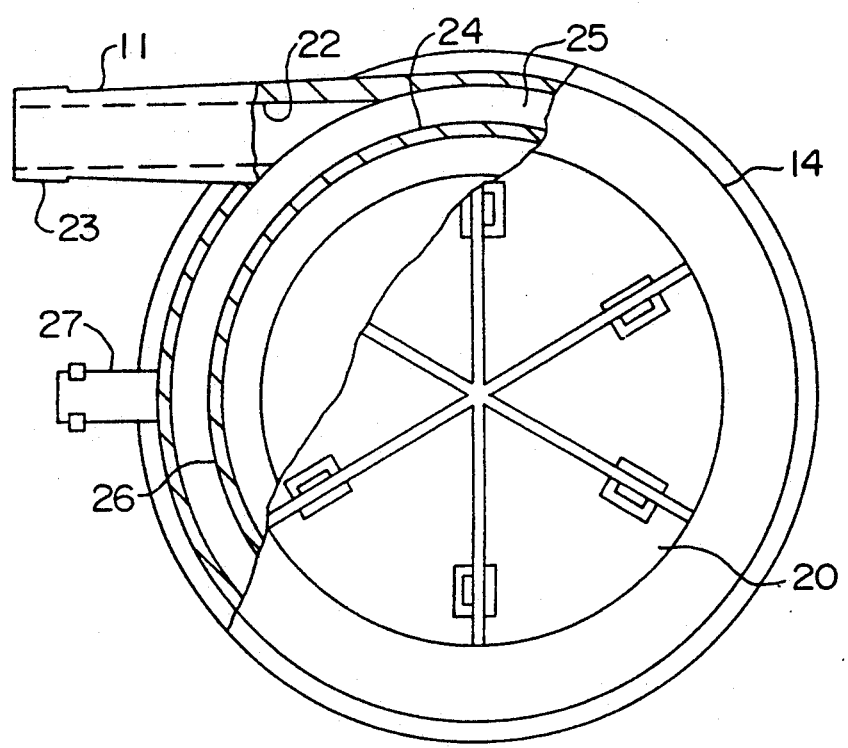
FIG. 2 is a top view of the filter assembly, including the cover and a top portion of the body of the housing.

Any housing of suitable shape to provide an inlet and an outlet for liquid and a space for a porous medium disposed between the inlet and outlet can be employed. A preferred embodiment of the filter assembly comprises a generally cylindrical housing 10 having an inlet 11 and an outlet 12, as shown in FIGS. 1 and 2. Housings can be designed to accept a variety of shapes of filter assemblies. For example, a square or octagon shaped housing and other possible forms designed to accommodate a similarly shaped porous medium would in principle all be functional, provided that adequate flow area is provided by the porous medium. These shapes are within the scope of the claimed invention.

Any housing of suitable configuration to reliably contain the liquid and define a liquid flow path through the porous medium can be employed. A preferred embodiment of the filter assembly comprises a housing 10 which generally includes two parts, a body 13 and a cover 14, and defines upper and lower chambers 15, 16. The cover 14 has a shallow, generally cylindrical configuration and includes a generally flat top wall 20 and a downturned, generally cylindrical side wall 21.

In a preferred embodiment, the cover 14 includes the inlet 11, as shown in FIG. 2. The inlet 11 may be variously configured. For example, the inlet 11 may comprise a nipple 23 which defines an inlet passage 22 and may be molded integrally with the cover 14. In the illustrated embodiment, the inlet 11 is configured to receive the end of a tube (not shown). In a preferred embodiment, the inlet passage 22 is horizontal and opens through the side wall of the cover 14 in a direction tangential to the side wall.

The cover 14 may also be provided with an accessory port 27 and an annular baffle 24. The accessory port 27 may be used to provide pressure measurements or samples of the liquid being filtered. When it is not in use, the accessory port 27 may be capped. The annular baffle 24 is preferably concentric with and spaced inwardly from the side wall 21. The baffle 24 may be formed integrally with the cover 14, extending downwardly from the top wall 20, and may be generally coextensive with the side wall 21, forming a circular channel portion 25 in the upper chamber 15. An opening 26 in the baffle 24 allows the circular channel 25 to communicate with a vent in the cover 14.

The vent allows gas to escape from the housing and may be configured in a variety of ways. For example, it may comprise a nipple with a manually operable valve. However, in a preferred embodiment, the vent comprises one or more holes 30 spaced around the top wall 20 of the cover 14. A porous, liquophobic membrane 31 may cover the holes 30 allowing gas but not liquid to escape from the housing. In a preferred embodiment, the liquophobic membrane may be attached to the underside of the top wall 20 of the cover 14 to allow a relatively free flow of gas from the housing. The liquophobic membrane may be variously configured. For example, it may comprise a polytetrafluoroethylene membrane having an absolute pore rating of about 0.2 $\mu$ and a polypropylene backing as a support.

The housing may be fabricated from any sufficiently rigid, impervious material which is compatible with the biological fluid. For example, the housing may be fabricated from a metal, such as stainless steel, or from a polymer. In a preferred embodiment, the housing is fabricated from a plastic material, such as polystyrene, polycarbonate, or polypropylene. In addition, all of the surfaces of the housing which contact the liquid are preferably liquophilic, i.e., readily wettable by the fluid. For example, the internal surfaces of the body 13 and the cover 14 may be treated to achieve a high degree of liquophilicity, e.g., by surface graft co-polymerization of hydroxyl functional monomers or by subjecting the internal surfaces to gas plasma treatment, as noted below. These liquophilic internal surfaces then readily facilitate the release of gas bubbles during the preparation and priming operation. A method of reducing the adhesion of bubbles in medical equipment is disclosed in U.S. Pat. No. 4,861,617.

The degassing element 50 may be fashioned from any material which causes small gas bubbles in the fluid to coalesce and separate from the fluid. In a preferred embodiment, the degassing element is a porous structure such as a porous foam or sponge material, and may include a rigid porous member 51 which engages the pleated porous medium. In addition, the degassing element may be treated with an anti-foaming agent to aid in breaking down the film between bubbles, for example, a compound of silicone and silica, such as Medical Antifoam A, available from Dow Corning Mfg. Co.

In accordance with one aspect of the invention, the porous medium may be fashioned to decrease the leucocyte content of a biological fluid which is passed through the porous medium. The porous medium may be fashioned in a variety of ways to effectively remove the leucocytes, as well as other deleterious matter from the liquid. In a preferred embodiment, the porous medium may be any medium or combination of media which maintain leukocyte removal without clogging. For example, the porous medium preferably comprises a fibrous structure made from any material compatible with the liquid and may be untreated or may be treated in a variety of ways to make the porous medium even more effective. The fibers may be bonded, fused, or otherwise fixed to one another or they may simply be mechanically entwined.

Further, the porous medium may be configured as a flat sheet, a corrugated or pleated member, and preferably also includes structures such as end caps, edge seals, a cage, a core, or a wrap. In a preferred embodiment, the porous medium also may include a downstream screen, preferably about a 40 micron screen, suitable for removing debris greater than about 40 microns.

Included within the scope of the present invention is a pleated fibrous porous medium having at least two layers of porous medium, the fibers of which may be microfibrous, woven, or unwoven, and in the form of a sheet, web, membrane, or the like.

As shown in FIG. 1, a preferred embodiment of the invention has a hollow, generally cylindrical configuration and comprises a pleated medium 53, a porous element or screen 54, a perforated core 55, an upper blind end cap 56, and a lower open end cap 57. The porous medium is preferably disposed within the lower chamber 16 in the housing 10 and is smaller in diameter than the side wall of the body 13 so that an annular space 60 is left between the side wall and the porous medium 36. The interior of the porous medium communicates with the centrally located outlet 12.

The porous element or screen 54, which preferably has a pore size no greater than about 40 microns, is disposed coaxially adjacent to the downstream surface of the pleated medium, e.g., around the interior of the pleated medium. The porous element 54 may be fashioned from any compatible porous membrane or woven or non-woven material, including a mesh or a screen. The porous element 54 serves principally as a final filter to remove, for example, any aggregates which escape the pleated medium or form at the downstream portion of the pleated medium.

The perforated core 55 is disposed within and adjacent to the interior of the porous element 54 and serves principally to support the pleated medium 53 and the porous element 54 against the differential pressure across the porous medium 36. Consequently, the perforated core 55 may be fashioned from any suitably rigid material including a metal such as stainless steel or a rigid polymer such as polyolefin, polyester, or polyacrylate.

The end caps 56, 57 serve to direct the liquid radially outside/in through the porous medium 36. Both end caps 56, 57 may be fashioned from any suitably impervious material, such as a metallic or polymeric material, preferably a polymer such as polypropylene, which is compatible with the fluid to be filtered; the end caps are fixed to the respective ends of the pleated medium, the porous element 54, and the perforated core 55. Alternatively, the lower ends of the pleated medium, the porous element, and the perforated core may be fixed directly to the bottom wall of the body, eliminating the need for a lower end cap. The end caps 56 and 57 may be secured to the ends of the porous medium by any suitable means, including a bonding agent such as an adhesive or a potting compound. Alternatively, the end caps 56 and 57 may be melt-bonded to the ends of the porous medium or joined by means of spin bonding or sonic welding. The ends of the hollow core 55 may be secured to the two end caps 56 and 57 by similar means.

A blind end cap 56 and an open end cap 57 may be fitted over the two ends of the porous medium to direct fluid through the porous medium. Alternatively, both end caps can be open or can include connectors to link a stack of porous media.

Alternatively, the porous medium may be designed for inside/out flow. The porous element may then be disposed around the exterior of the fibrous mass, the upper end cap may be an open end cap, and the lower end cap may be a blind end cap. The core may be omitted but a cage disposed coaxially around the porous element to support the fibrous mass and the porous element against the pressure drop may be added. Of course, the housing would be rearranged to permit the inlet to communicate with the interior of the porous medium and the outlet to communicate with the exterior of the porous medium.

Polymeric materials particularly well suited for the fibrous medium include, but are not limited to thermoplastics such as the polyolefins, particularly polypropylene and polymethylpentene; polyamides, particularly nylon 6, nylon 610, nylon 10, nylon 11, nylon 12; and polyesters, particularly polybutylene terephthalate and polyethylene terephthalate. Other suitable, but less preferred, polymers are addition polymers such as polyvinyl fluoride, polyvinylidene fluoride and their copolymers. The preferred material is polybutylene terephthalate.

In the illustrated embodiment, the annular thickness of the pleated structure of a fibrous medium is preferably in the range from 0.1 to about 3 inches (0.25 cm to 7.62 cm), more preferably in the range from about 0.2 to about 0.8 inch (0.51 to 2.0 cm), and most preferably in the range from about 0.3 to about 0.6 inch (0.76 to 1.52 cm). The outer diameter of the fibrous medium is preferably less than about 8.5 inches (21.6 cm), more preferably less than about 3 inches (7.62 cm). The height of the pleated structure is preferably up to about 5.5 inches (14 cm), more preferably about 2.5 inches (6.4 cm). The hold up volume of the filter assembly is preferably up to about 1 liter, more preferably, up to about 5.1, most preferably 100 ccs to 250 ccs.

In a preferred embodiment, the fibrous medium may be formed into a sheet; multiple sheets may then be layered and pleated using conventional pleating equipment. The pleated structure typically includes about 4-16 pleats per inch, preferably about 10 pleats per inch. The height of the pleats are typically about 0.2 to about 0.6 inch, preferably about 0.4 inch.

Although the fibers of the fibrous medium may remain untreated, they are preferably treated to make them even more effective for removing leucocytes and other deleterious matter. For example, the fibers may be surface modified to increase the critical wetting surface tension (CWST) of the fibers, in addition to affecting other characteristics of the fibers.

As disclosed in U.S. Pat. No. 4,880,548, the CWST of a porous medium may be determined by individually applying to its surface a series of liquids with surface tensions varying by 2 to 4 dynes/cm and observing the absorption or non-absorption of each liquid over time. The CWST of a porous medium, in units of dynes/cm, is defined as the mean value of the surface tension of the liquid which is absorbed and that of the liquid of neighboring surface tension which is not absorbed within a predetermined amount of time. The absorbed and non-absorbed values depend principally on the surface characteristics of the material from which the porous medium is made and secondarily on the pore size characteristics of the porous medium.

Surface characteristics of a fiber can be modified by a number of methods, for example, by chemical reaction including wet or dry oxidation, by coating the surface by depositing a polymer thereon, and by grafting reactions which are activated by exposure to an energy source such as heat, a Van der Graff generator, ultraviolet light, or to various other forms of radiation. In accordance with the present invention, the preferred method is by gas plasma treatment (GPT).

In accordance with the present invention, the fibrous medium, either pleated or unpleated, can be improved or modified when the surface of the fiber is treated with or exposed to low temperature gas plasma with or without deposition of a polymeric substance formed by the plasma or introduced into the plasma.

The term "plasma" or "gas plasma" is used generally to describe the state of ionized gas. A plasma consists of high energy charged ions (positive or negative), negatively charged electrons, and neutral species. As known in the art, a plasma may be generated by combustion, flames, physical shock, or, preferably, by electrical discharge, such as a corona or glow discharge. In radiofrequency (RF) discharge, a substrate to be treated is placed in a vacuum chamber and gas at low pressure is bled into the system. An electromagnetic field is generated by subjecting the gas to a capacitive or inductive RF electrical discharge. The gas absorbs energy from the electromagnetic field and ionizes, producing high energy particles. These high energy particles are used to modify the surface of the fibers or medium.

For plasma treatment of the fibers or medium, typically the GPT apparatus is evacuated by attaching a vacuum nozzle to a vacuum pump. Gas from a gas source is bled into the evacuated apparatus through the gas inbleed until the desired gas pressure differential across the conduit is obtained. An RF electromagnetic field is generated in the plasma zone by applying current of the desired frequency to the electrodes from the RF generator. Ionization of the gas in the tube is induced by the field, and the resulting plasma in the tube modifies the fibers or medium in the plasma zone.

The gas used to treat the surface of the fiber or medium may include inorganic or organic gases. Inorganic gases are exemplified by helium, argon, nitrogen, neon, nitrous oxide, nitrogen dioxide, oxygen, air, ammonia, carbon monoxide, carbon dioxide, hydrogen, chlorine, hydrogen chloride, bromine cyanide, sulfur dioxide, hydrogen sulfide, xenon, krypton, and the like. Organic gases are exemplified by acetylene, pyridine, gases of organosilane compounds and organopolysiloxane compounds, fluorocarbon compounds and the like. In addition, the gas may be a vaporized organic material, such as an ethylenic monomer to be plasma polymerized or deposited on the surface of the fiber. These gases may be used either singly or as a mixture of two kinds or more according to need. The preferred gas according to the present invention is oxygen.

Typical parameters for treatment of the fibers or medium with a gas plasma may include power levels from about 10 watts to about 3000 watts, preferably 500 watts to about 2500 watts; RF frequency of about 1 kHz to 100 MHz, preferably about 15 kHz to about 50 MHz; exposure times of about 5 seconds to 12 hours, preferably about 1 minute to 2 hours; gas pressures of about 0.001 to 100 torr, preferably about 0.01 to 1 torr; and a gas flow rate of about 1 to about 2000 standard cc/min.

The flow rate of liquid passing through a filter assembly of the present invention can vary according to the particular use and for any given patient, but the flow rate should be maintained at a level which does not harm or destroy erythrocytes or platelets in the liquid.

While the devices described herein are principally directed to a filter assembly having a capacity of passing up to about 6 liters/minute, filter assemblies having a larger or smaller capacity can be made. Included within the scope of the invention is a filter assembly designated as a "low flow" size, which has a flow rate of about 3 liters/minute or less, has approximately one-third the fiber surface area and about one-half the capacity of the adult device.

A filter assembly according to the present invention has the capacity for up to about 10 hours of continuous removal of a clinically or therapeutically significant amount of leucocytes and other deleterious matter from a biological fluid. However, many of the uses for which these filter assemblies are suitable do not require 10 hours of filtration. For example, a cardiac bypass operation may only require 6-8 hours; cardioplegia may require only 2-4 minutes of filtration. Some therapeutic protocols performed under emergency conditions require only 10-20 seconds of filtration, or several periodic or repeated filtrations of about 10-20 seconds duration.

A filter assembly in accordance with the present invention is capable of decreasing the leucocyte content of the biological fluid. This generally means removing a therapeutically or clinically significant amount of leucocytes from a biological fluid. "Therapeutically or clinically significant amount" refers an amount necessary to produce a beneficial effect on the patient or animal receiving the leucocyte depleted liquid. Such a beneficial effect may be, for example, lessening reperfusion injury. A therapeutically or clinically significant amount can vary depending on the intended use and/or from patient to patient. For example, a therapeutically or clinically significant amount can be greater for a cardiac bypass procedure than for cardioplegia. However, removal of a therapeutically or clinically significant amount can be and is routinely determined by a doctor or technician for treating a certain condition or disease as it pertains to the specific patient or animal, and as it pertains to the particular application.

A filter assembly of the present invention may be used in any procedure, therapy, operation, or environment in which the removal of activated leucocytes and deleterious matter is desirable or beneficial. Because leucocytes have the potential for becoming activated upon contact with almost anything ex-vivo, many applications exist for the use of the filter assemblies of the present invention in reducing the number of activated leucocytes. While the filter assembly of the present invention is particularly suited for treating reperfusion-induced injury and/or achieving leucocyte content equilibrium in an extracorporeal system, one skilled in the art will recognize other contexts in which removal of leucocytes and other deleterious matter in a liquid is desirable. Without intending to limit the invention thereby, the following provides examples of such uses.

EXAMPLES

Example 1

A filter assembly in accordance with the invention was produced as follows: polybutylene terephthalate (PBT) was formed into fibers by melt blowing, i.e., exposing molten PBT resin to a high velocity stream of gas, until 7.5 gm/ft$^2$ (80.7 gm/m$^2$) of fibers having an average diameter of 2.0 microns was obtained. Four layers were formed over a layer of 40 micron opening woven polyester mesh. These five layers were pleated together with an extruded polypropylene mesh having a thickness of 0.02 inch (0.05 cm) and openings of about 0.06 inch (0.15 cm) by 0.06 inch (0.15 cm). The pleats were formed using conventional pleating equipment having heated platens to maintain the pleated structure to form a structure having 10 pleats per inch (2.54 cm) and a height of about 0.4 inch (1.02 cm).

The pleated media assembly was cut to a length of 2.5 inches (6.35 cm) and a width of 4 inches (10.16 cm), i.e., about 40 pleats. The assembly was formed into a cylindrical structure and the ends were sealed using a conventional heat sealer. The dimensions of the cylindrical pleated structure were about 1.4 inches (3.56 cm) inside diameter by 2.2 inches (5.59 cm) outside diameter by 2.5 inches (6.35 cm) length. A 1.3 inches (3.30 cm) outside diameter by 2.5 inches (6.35 cm) length polypropylene core was placed inside the pleated cylinder, and polypropylene end caps were heat welded to the ends of the cylinder.

The filter assembly was then subjected to gas plasma treatment by exposing the assembly, in a B-series gas plasma generator obtained from Advanced Plasma Systems, Inc., to an $O_2$ plasma under the following conditions: 2.0 kilowatts, 40 kilohertz for 20 minutes and 150 mtorr $O_2$. The filter assembly was then assembled into a housing in preparation for testing for leucocyte removal from blood.

Example 2

This Example illustrates the use of the gas plasma treated porous medium of Example 1 in an extracorporeal circuit for the removal of leucocytes from blood. This test was designed to expose recirculating blood to the conditions typical of those encountered during cardio-pulmonary bypass surgery: an extracorporeal circuit having a pump, filter, pressure gauge, and reservoir; a blood flow rate of 3-6 liters per minute was maintained throughout the test; and recirculating the blood for about three hours. Blood samples were taken and the differential pressure across the filter was measured at various times during the test.

Six units of type-matched packed red cells to which the anti-coagulant Adsol ™ had been added were placed in the reservoir. After the filter and circuit were primed, blood in the resevoir was recirculated through the system at a flow rate of 3-6 liter per minute.

From samples of blood taken at various intervals during the test, it was found that the total leucocyte removal (neutrophils and lymphocytes), using a gas plasma treated porous medium produced as described in Example 1, was 39% after 1 hour of recirculation and 59% after 3 hours, the conclusion of the test. The pressure differential was less than 2 psi throughout the test.

By comparison a porous medium prepared with radiation grafted fibers and of the same construction as the gas plasma treated porous medium, leucocyte removal was 29% after 1 hour and 36% after 3 hours. These results illustrate the ability of the gas plasma treated porous medium of the present invention to remove leucocytes effectively while maintaining a desirably low pressure drop.

Example 3

A web of melt blown PBT microfibers having an average fiber diameter of about 2.4 microns was prepared as described in Example 1. The PBT web was formed into a multilayered structure having a total of 52 grams/ft$^2$ of the above media. A PBT porous medium (untreated) having a final thickness of about 0.08 inch was formed by heating the multilayered structure to a temperature of about 170° C. and applying pressure.

A portion of the PBT porous medium (untreated) was subjected to treatment with gas plasma with oxygen using the following conditions: 40 kHz radio frequency at 2000 watts for 15 minutes. The oxygen ($O_2$) pressure was 115 mtorr. The treated porous medium is referred to herein as the GPT porous medium. The remainder of the PBT porous medium (untreated) was used for comparative testing.

The GPT porous medium was then tested for platelet loss from both packed red cells and platelet concentrate. To carry out the testing, samples of the GPT porous medium were cut into a 0.94 inch diameter disc, and sealed in a reuseable plastic housing. The housing included an inlet port and an outlet port and defined a liquid flow path between the inlet and the outlet through the GPT porous medium.

TEST WITH BLOOD

Packed Red Cells (CPD anticoagulated with AS-1 additive solution) were obtained through standard processing means. The PRC had an age of 3 days. PRC was passed through a test housing containing GPT porous medium under gravity head pressure at an initial flow rate of 1 cc/min. The leucocyte and platelet concentration in the filtrate was measured and compared to the unfiltered PRC. The results showed average leucocyte removal of 99.7% and an average platelet loss of 22%. For comparison, a similar test was conducted with PRC and a sample of PBT porous medium (untreated). The results showed a platelet loss of 99% for the same PBT porous medium without GPT surface modification.

The test illustrates the surprising ability for the GPT porous medium to pass a high proportion of platelets contained in blood.

We claim:

1. A leucocyte depletion filter assembly for removing leucocytes and other deleterious mater from a biological fluid in an extracorporeal circuit, the filter assembly comprising:
   a housing having an inlet and an outlet and defining a liquid flow path between the inlet and the outlet, and
   a pleated medium positioned inside the housing across the liquid flow path and including a fibrous means for decreasing the leucocyte content of the liquid, the surface of said fibrous means being modified by exposure to a gas plasma stream, wherein said fibrous means is capable of permitting the passage of red blood cells and platelets therethrough.

2. The leucocyte depletion filter assembly of claim 1 having a capacity of six liters per minute at a differential pressure less than 15 psi.

3. The leucocyte depletion filter assembly of claim 1 having a hold up volume in the range from about 70 cc to about 400 cc.

4. The leucocyte depletion filter assembly of claim 1 wherein the fibrous means has a hollow, generally cylindrical configuration.

5. The leucocyte depletion filter assembly of claim 1 wherein the fibrous means has a CWST of at least 52 dynes/cm.

6. The leucocyte depletion filter assembly of claim 1, wherein said gas plasma is generated from an inorganic gas.

7. The leucocyte depletion filter assembly of claim 1, wherein said gas plasma is generated from an organic gas.

8. The leucocyte depletion filter assembly of claim 1, wherein said gas plasma is generated from a gas selected from the group consisting of helium, argon, nitrogen, neon, nitrous oxide, nitrogen dioxide, oxygen, air, ammonia, carbon monoxide, carbon dioxide, hydrogen, chlorine, hydrogen chloride, bromine cyanide, sulfur dioxide, hydrogen sulfide, xenon, krypton, and mixtures thereof.

9. The leucocyte depletion filter assembly of claim 8, wherein said gas is oxygen.

10. The leucocyte depletion filter assembly of claim 1, wherein said pleated medium is of fibers of a synthetic resin.

11. The leucocyte depletion filter assembly of claim 10, wherein said synthetic resin is a member selected from the group consisting of polyolefin, polyesters, polysulfones, polyamides, acrylics, polyarylene oxides, polyarylene sulfides, and polymers and copolymers made from halogenated olefins.

12. The leucocyte depletion filter assembly of claim 11, wherein said synthetic resin is a polyester.

13. The leucocyte depletion filter assembly of claim 12, wherein said polyester is polybutylene terephthalate.

14. The leucocyte depletion filter assembly of claim 13, wherein said pleated medium has been treated with an oxygen gas plasma at about 40 kilohertz, about 2 kilowatts, and about 100–150 mtorr for about 10–30 minutes.

15. The leucocyte depletion filter assembly of claim 1, wherein said plated medium has been treated with a gas plasma at about 10 to about 3000 watts, about 1 kHz to about 100 MHz, and about 0.001 to 100 torr for about 5 seconds to about 12 hours.

16. The leucocyte depletion filter assembly of claim 15, wherein said pleated medium has been treated with a gas plasma at about 500 to about 2500 watts, about 15 kHz to about 60 MHz, and about 0.01 to 1 torr for about 1 minute to about 2 hours.

17. The leucocyte depletion filter assembly of claim 16, wherein said pleated medium has been treated with a gas plasma at about 1500 to about 2500 watts, about 30 kHz to about 50 kHz, and about 0.1 to 1 torr for about 10 minutes to about 30 minutes.

18. The leucocyte depletion filter assembly for removing leucocytes and other deleterious matter from a biological fluid in an extracorporeal circuit, the filter assembly comprising:
   a housing having an inlet, an outlet, and a vent and defining a liquid flow path between the inlet and the outlet;
   a degassing mechanism communicating with the vent for removing gas from the biological fluid; and
   a pleated fibrous medium positioned in the housing across the liquid flow path, the surface of said fibrous medium having been modified by exposure to a gas plasma stream, said fibrous medium being capable of decreasing the leucocyte consent of the biological fluid and permitting the passage of red cells and platelets therethrough.

19. The leucocyte depletion filter assembly of claim 18 having a capacity of six liters per minute at a differential pressure less than 15 psi and having a hold up volume in the range from about 70 cc to about 400 cc.

20. A leucocyte depletion filter assembly for removing leucocytes and other deleterious matter from a biological fluid in an extracorporeal circuit, the filter assembly comprising:
   a generally cylindrical housing having first and second chambers, an inlet which allows tangential inflow into the first chamber, an outlet which allows outflow from the second chamber, and a vent;
a porous degassing element position end between the first and second chambers to remove gas from the biological fluid;
a liquophobic membrane covering the vent and communicating with the degassing element to allow gas but not liquid to flow through event; and
a hollow, cylindrical porous medium positioned in the second chamber and comprising a pleated fibrous medium having a CWST of 52 dynes/cm or greater, the surface of said fibrous medium having been modified by exposure to a gas plasma stream, said fibrous medium being capable of decreasing the leucocytes content of the biological fluid and permitting the passage of red cells and platelets therethrough, and the interior of the hollow pours medium communicating with the outlet.

21. A method for removing leucocytes and other deleterious matter from a biological fluid comprising:
passing the biological fluid through a pleated fibrous medium in an extracorporeal circuit, the surface of the fibrous medium having been modified by exposure to a gas plasma stream, said fibrous medium being capable of decreasing the leucocytes content of the biological fluid and permitting the passage of red cells and platelets therethrough.

22. The method of claim 21 wherein up to six liters per minute of biological fluid are placed through the fibrous medium.

23. The method of claim 21, wherein said gas plasma is generated from a gas selected from the group consisting of helium, argon, nitrogen, neon, nitrous oxide, nitrogen dioxide, oxygen, air, ammonia, carbon monoxide, carbon dioxide, hydrogen, chlorine, hydrogen chloride, bromine cyanide, sulfur dioxide, hydrogen sulfide, xenon, krypton, and mixtures thereof.

24. The method of claim 21, wherein aid pleated medium has been treated with a gas plasma at about 10 to about 3000 watts, about 1 kHz to about 100 MHz, and about 0.001 to 100 torr for about 5 seconds to about 12 hours.

25. The method of claim 21, wherein the fibrous medium comprises a synthetic resin selected from the group consisting of polyolefins, polyesters, polysulfones, polyaramides, acrylics, polyarylene oxides, polyarylene sulfides, and polymers and copolymers made from halogenated olefins.

26. The method of claim 25, wherein said polyester is polybutylene terephthalate.

27. The method of claim 26, wherein said pleated medium has been treated with an oxygen gas plasma at about 40 kilohertz, about 2 kilowatts, and about 100–150 mtorr for about 10–30 minutes.

28. A method for removing leucocytes and other deleterious matter from a biological fluid comprising:
directing biological fluid in an extracorporeal circuit through a housing;
separating gas for the biological fluid;
venting the gas for the housing;
passing the biological fluid through a fibrous means positioned within the housing, the surface of said fibrous means having been modified by exposure to a gas plasma stream, thereby decreasing the leucocyte content of the biological fluid while permitting the passage of red blood cells and platelets.

29. The method of claim 28 wherein directing the fluid through a housing comprises repeatedly circulating the biological fluid through the housing.

30. A method of treating blood in an extracorporeal circuit comprising:
directing the blood through a housing;
separating gas from the blood;
venting the gas from the housing;
passing the blood through a fibrous medium positioned within the housing, the surface of said fibrous medium having been modified by exposure to a gas plasma stream, thereby decreasing the leucocyte consent of the blood while permitting the passage of red blood cells and platelets.

31. A method for removing leucocytes and other deleterious matter from a biological fluid comprising:
directing biological fluid in an extracorporeal circuit through a pleated fibrous medium which allows platelets and red cells to pass therethrough, at a flow rate of up to six liters per minute, the surface of said fibrous medium having been modified by exposure to a gas plasma stream; and
removing a clinically or therapeutically significant amount of leucocytes from the biological fluid.

32. The method of claim 31 wherein directing the fluid through a housing comprises repeatedly circulating the biological fluid through the housing.

* * * * *

UNITED STATES PATENT AND TRADEMARK OFFICE
CERTIFICATE OF CORRECTION

PATENT NO. : 5,258,127
DATED : November 2, 1993
INVENTOR(S) : Gsell et al.

It is certified that error appears in the above-indentified patent and that said Letters Patent is hereby corrected as shown below:

Title Page:
In item no. [56], References Cited, Other Publications, the following were omitted:

--"The Pall EC Plus Filter", A New Generation Extracoporeal Filter Pall et al., pp. 3-7.

"Bibliography of Swank Blood Filters for Extracorporeal Circulation", Swank et al.

"AutoVent-SP", Auto-Venting Blood Filter, Biomedical Products Corporation, Pall et al.

Disposable Filter For Microemboli", Journal of the American Medial Association, Patterson et al., January 4, 1971, vol. 215, pp. 76-80.

"Performance Characteristics of Bentley Duraflo II Treated Arterial Filters", Baxter Healthcare Corporation, pp. 3-11.

"Plasma Deposition, Treatment, and Etching of Polymers", Riccardo d' Agostino, Academic Press, Inc., 1990, pp. 463-516.

S. Karger, "Journal of Blood Transfusion, etc., Vox Sanguinis, Vox Sang.23: (1972), pp. 308-320.--

UNITED STATES PATENT AND TRADEMARK OFFICE
CERTIFICATE OF CORRECTION

PATENT NO. : 5,258,127
DATED : November 2, 1993
INVENTOR(S) : Gsell et al.

It is certified that error appears in the above-indentified patent and that said Letters Patent is hereby corrected as shown below:

Claim 1, column 11, line 35, change "mater" to --matter--.

Claim 15, column 12, line 29, change "plated" to --pleated--.

Claim 18, column 12, line 43, change "The" to --A--;

Claim 18, column 12, line 56, change "consent" to --content--.

Claim 20, column 13, line 3, change "position end" to --positioned--;

Claim 20, column 13, line 8, change "event" to --the vent--;

Claim 20, column 13, line 17, change "pours" to --porous--.

Claim 22, column 13, line 29, change "placed" to --passed--.

Claim 24, column 13, line 39, change "aid" to --said--.

UNITED STATES PATENT AND TRADEMARK OFFICE
CERTIFICATE OF CORRECTION

PATENT NO. : 5,258,127

DATED : November 2, 1993

INVENTOR(S) : Gsell et al

It is certified that error appears in the above-indentified patent and that said Letters Patent is hereby corrected as shown below:

Claim 30, column 14, lin 33, change "consent" to --content--.

Signed and Sealed this

Seventh Day of June, 1994

Attest:

BRUCE LEHMAN

Attesting Officer

Commissioner of Patents and Trademarks